US008620698B2

(12) United States Patent
Hu et al.

(10) Patent No.: US 8,620,698 B2
(45) Date of Patent: *Dec. 31, 2013

(54) SYSTEM AND METHOD FOR CALCULATING ESTIMATED CLAIM COSTS

(71) Applicant: Hartford Fire Insurance Company, Hartford, CT (US)

(72) Inventors: Wangyang Hu, Burlington, CT (US); Kathleen F. Maurer, Westbrook, CT (US); Kelly J. McLaughlin, Cobalt, CT (US)

(73) Assignee: Hartford Fire Insurance Company, Hartford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/909,243

(22) Filed: Jun. 4, 2013

(65) Prior Publication Data

US 2013/0290037 A1    Oct. 31, 2013

Related U.S. Application Data

(63) Continuation of application No. 13/348,175, filed on Jan. 11, 2012, now Pat. No. 8,457,984, which is a continuation of application No. 12/466,016, filed on May 14, 2009, now Pat. No. 8,117,043.

(51) Int. Cl.
*G06Q 10/00* (2012.01)
*G06Q 40/00* (2012.01)
*G06Q 50/00* (2012.01)

(52) U.S. Cl.
USPC .......... 705/4; 705/2; 705/3; 705/35

(58) Field of Classification Search
USPC .................. 705/2–4, 35
See application file for complete search history.

(56) References Cited

U.S. PATENT DOCUMENTS

| | | | |
|---|---|---|---|
| 7,127,407 B1* | 10/2006 | Averill et al. | 705/2 |
| 7,389,245 B1* | 6/2008 | Ashford et al. | 705/2 |
| 2005/0091083 A1 | 4/2005 | McGuigan et al. | |
| 2005/0203773 A1 | 9/2005 | Soto et al. | |
| 2008/0147448 A1 | 6/2008 | McLaughlin et al. | |
| 2009/0043615 A1 | 2/2009 | Belhe et al. | |

OTHER PUBLICATIONS

Franklin, Gary M. et al., "Outcome of Lumbar Fusion in Washington State Workers' Compensation", SPINE vol. 19, No. 17, 1994, J. B. Lippincott Company, pp. 1897-1903 (7 pages total).

(Continued)

*Primary Examiner* — Joseph Burgess
(74) *Attorney, Agent, or Firm* — Howard IP Law Group, PC

(57) ABSTRACT

A computer system includes a data storage device. The data storage module receives, stores, and provides access to historical claim data. A categorical aggregation component comprising program instructions stored in a program memory provides categorized and aggregated historical claim data by identifying claim categories based on the historical claim data, each of the one or more claim categories associated with a respective set of claim characteristics, identifying claims of the historical claim data associated with one of the claim categories, assigning each identified claim to one of a plurality of total severity ranges based on the total severity of the identified claim, and determining an average cost per claim year for claims of each total severity range when executed by a computer processor.

20 Claims, 11 Drawing Sheets

(56) References Cited

OTHER PUBLICATIONS

Juratli, Sham Maghout et al., "Lumbar Fusion Outcomes in Washington State Workers' Compensation", vol. 31 (23), Nov. 1, 2006, Lippincott Williams & Wilkins, Inc., 20 pgs.

LaCaille, Rick A. et al., "Obesity and litigation predict workers' compensation costs associated with interbody cage lumbar fusion", The Spine Journal 7 (2007), pp. 266-272 (7 pages total).

LaCaille, Rick A. et al., "Presurgical biopsychosocial factors predict multidimensional patient: outcomes of interbody cage lumbar fusion", The SPINE Journal 5 (2005), pp. 71-78 (8 pages total).

Turner, Judith A. et al., "Worker Recovery Expectations and Fear-Avoidance Predict Work Disability in a Population-Based Workers' Compensation Back Pain Sample", vol. 31(6), Mar. 15, 2006, Lippincott Williams & Wilkins, Inc., 15pgs.

DeBerard, M. Scott et al., "Outcomes of Posterolateral Lumbar Fusion in Utah Patients Receiving Workers' Compensation", Spine vol. 26, No. 7, 2001, Lippincott Williams & Wilkins, Inc., pp. 738-747 (10 pages total).

* cited by examiner

Severity Range: Top 20%
Category: Non-traumatic Lumbar Surgery
Expense Category: Hospital

| | 1 | 2 | 3 | 4 | 5 | 6 | 7 | 8 | 9 | 10 |
|---|---|---|---|---|---|---|---|---|---|---|
| 1998 | 24,706 | 11,154 | 9,610 | 7,964 | 11,251 | 7,013 | 7,063 | 12,298 | 14,953 | 7,818 |
| 1999 | 22,848 | 11,548 | 9,725 | 8,354 | 6,742 | 5,756 | 9,960 | 7,957 | 12,032 | |
| 2000 | 17,937 | 12,250 | 10,743 | 7,437 | 10,466 | 11,255 | 8,687 | 5,469 | | |
| 2001 | 18,537 | 11,088 | 10,771 | 5,506 | 6,265 | 8,550 | 7,845 | | | |
| 2002 | 20,550 | 11,991 | 11,776 | 10,430 | 5,689 | 6,682 | | | | |
| 2003 | 22,993 | 9,938 | 10,889 | 14,718 | 10,441 | | | | | |
| 2004 | 20,669 | 10,901 | 8,999 | 7,862 | | | | | | |
| 2005 | 23,690 | 11,016 | 8,511 | | | | | | | |
| 2006 | 21,213 | 10,128 | | | | | | | | |
| 2007 | 23,506 | | | | | | | | | |
| Average Cost | 21,659 | 11,113 | 10,128 | 8,896 | 8,476 | 7,851 | 8,389 | 8,575 | 13,493 | 7,818 |

FIG. 4

Severity Range    Middle 60%
Category          Non-traumatic Lumbar Surgery
Expense Category  Hospital

| | 1 | 2 | 3 | 4 | 5 | 6 | 7 | 8 | 9 | 10 |
|---|---|---|---|---|---|---|---|---|---|---|
| 1998 | 160 | 124 | 82 | 64 | 45 | 34 | 27 | 24 | 20 | 18 |
| 1999 | 156 | 123 | 80 | 53 | 33 | 28 | 26 | 16 | 22 | |
| 2000 | 152 | 122 | 74 | 49 | 34 | 22 | 14 | 12 | | |
| 2001 | 211 | 166 | 105 | 70 | 56 | 45 | 39 | | | |
| 2002 | 195 | 158 | 108 | 79 | 68 | 52 | | | | |
| 2003 | 176 | 142 | 93 | 56 | 42 | | | | | |
| 2004 | 185 | 153 | 96 | 61 | | | | | | |
| 2005 | 189 | 127 | 72 | | | | | | | |
| 2006 | 203 | 150 | | | | | | | | |
| 2007 | 183 | | | | | | | | | |
| Grand Total | 1810 | 1265 | 710 | 432 | 278 | 181 | 106 | 52 | 42 | 18 |

| | 2 | 3 | 4 | 5 | 6 | 7 | 8 | 9 | 10 |
|---|---|---|---|---|---|---|---|---|---|
| 1998 | 77.5% | 51.3% | 40.0% | 28.1% | 21.3% | 16.9% | 15.0% | 12.5% | 11.3% |
| 1999 | 78.8% | 51.3% | 34.0% | 21.2% | 17.9% | 16.7% | 10.3% | 13.3% | |
| 2000 | 80.3% | 48.7% | 32.2% | 22.4% | 14.5% | 9.2% | 7.9% | | |
| 2001 | 78.7% | 49.8% | 33.2% | 26.5% | 21.3% | 18.5% | | | |
| 2002 | 81.0% | 55.4% | 40.5% | 34.9% | 26.7% | | | | |
| 2003 | 80.7% | 52.8% | 31.8% | 23.9% | | | | | |
| 2004 | 82.7% | 51.9% | 33.0% | | | | | | |
| 2005 | 67.2% | 38.1% | | | | | | | |
| 2006 | 73.9% | | | | | | | | |
| Grand Total | 77.8% | 49.9% | 35.0% | 26.2% | 20.3% | 15.3% | 11.1% | 12.9% | 11.3% |

FIG. 5

| Claimant | Name | | Fusion? | Y |
|---|---|---|---|---|
| Claim # | XYZ C 12345 | | Surgery location | Lumbar |
| Birthdate | 04-16-1962 | | First Surgery Date | 1/1/2008 |
| Valuation Date | 03-27-2009 | | Years Post Surgery | 1 |
| Sex | F | | | |
| Medical Age | - | | | |
| Valuation Age | Real Age | | | |
| Age at Valuation | 47 | | | |
| Life Expectancy | 34.96 | | | |

| Projected Annual Spend | |
|---|---|
| H | |
| P | |
| R | |
| OM | |

Obesity

| Height (feet) | 5 |
|---|---|
| Height (inches) | 3 |
| Weight (lbs) | 225 |
| Obesity | Y |

| Drugs/Alcohol | N |
|---|---|
| Psych | Y |
| Medical Discount | 5.00% |

| High Misc Ex | # of years anticipated | In ? years | Cost/year | Inflation rate | Total Cost | PCV |
|---|---|---|---|---|---|---|
| | | | | | | |

Total Misc. Exposure

| Low Misc Ex | # of years anticipated | In ? years | Cost/year | Inflation rate | Total Cost | PCV |
|---|---|---|---|---|---|---|
| | | | | | | |

Total Misc. Exposure

*FIG. 8*

| | | | Hospital Costs | | | Physician Costs | | | Drug Costs | | | Other Medical Costs | | | Co-morbidities | | | | | |
|---|---|---|---|---|---|---|---|---|---|---|---|---|---|---|---|---|---|---|---|---|
| Outcome Scenario | Natural Medical Closure? | Cost | 1st Year | Annual | Total | 1st Year | Annual | Total | 1st Year | Annual | Total | 1st Year | Annual | Total | Obesity | Alcohol | Psych | Total Reserve | LHood | Wghtd Total |
| 1 | No | High | 14,311 | 14,311 | 245,935 | 9,061 | 9,061 | 155,720 | 3,863 | 4,436 | 149,919 | 17,717 | 17,717 | 304,468 | 1.1252 | .9620 | 1.1396 | 856,041 | 17% | 146,140 |
| 2 | No | Med | 1,238 | 1,238 | 21,275 | 2,306 | 2,306 | 39,625 | 1,325 | 2,016 | 64,267 | 2,121 | 2,121 | 36,444 | 1.1252 | .9620 | 1.1396 | 161,612 | 8% | 12,142 |
| 3 | No | Low | 185 | 185 | 3,188 | 652 | 652 | 11,198 | 247 | 171 | 6,660 | 498 | 498 | 8,567 | 1.1252 | .9620 | 1.1396 | 29,613 | 0% | 57 |
| 4 | Yes | High | 14,311 | 14,311 | 70,536 | 9,061 | 9,061 | 44,662 | 3,863 | 4,436 | 16,520 | 17,717 | 17,717 | 87,324 | 1.1252 | .9620 | 1.1396 | 219,043 | 23% | 50,223 |
| 5 | Yes | Med | 1,238 | 1,238 | 3,960 | 2,306 | 2,306 | 7,376 | 1,325 | 2,016 | 3,043 | 2,121 | 2,121 | 6,784 | 1.1252 | .9620 | 1.1396 | 21,164 | 44% | 9,415 |
| 6 | Yes | Low | 185 | 185 | 496 | 652 | 652 | 1,741 | 247 | 171 | 566 | 498 | 498 | 1,332 | 1.1252 | .9620 | 1.1396 | 4,135 | 8% | 323 |

Fusion? Y
Surgery location: Lumbar
First Surgery Date: 1/1/2008
Years Post Surgery: 1

Duration: 34.96
Obesity: Y
Drugs/Alcohol: N
Psych: Y

Projected Annual Spend
| H | |
| P | |
| R | |
| OM | |

SYSTEM AND METHOD FOR CALCULATING ESTIMATED CLAIM COSTS

RELATED APPLICATIONS

This application is a continuation of co-pending U.S. patent application Ser. No. 13/348,175, filed Jan. 11, 2012, titled System For Evaluating Potential Claim Outcomes Using Related Historical Data, now U.S. Pat. No. 8,457,984, which is a a continuation of U.S. patent application Ser. No. 12/466,016, filed May 14, 2009, titled System For Evaluating Potential Claim Outcomes Using Related Historical Data, now U.S. Pat. No. 8,117,043, the entirety of each of which is incorporated by reference herein for all purposes.

FIELD

Embodiments relate to computer systems to categorize and aggregate historical claim data. Embodiments are also concerned with the evaluation of current claims based on categorized and aggregated historical claim data.

BACKGROUND

Insurance claims having multiple potential outcomes are difficult to evaluate. In the case of medical claims, for example, the extent of a claimant's future medical recovery is both indeterminate and inversely related to total claim cost (i.e., total severity).

According to existing techniques for evaluating a claim having multiple potential outcomes, an adjuster determines a most probable outcome based on her professional experience and based on the file history of the subject claim. A total severity is then estimated based on the determined outcome. The adjuster may use the estimated total severity as a basis for adjusting insurance reserves, suggesting treatment options, reallocating resources (e.g., triggering a nursing assignment or physician review), and/or re-assigning the claim to a more (or less) senior adjuster.

Conventional evaluation techniques do not provide a robust system to determine relative likelihoods of potential outcomes in order to identify a most probable outcome.

Conventional techniques also exhibit difficulty in estimating the total severity of an identified most probable outcome. Moreover, any actions performed by an adjuster based on the estimated total severity fail to take into account outcomes which present a lower probability but a higher exposure than the determined most probable outcome, and outcomes which present a lower probability and a lower exposure than the determined most probable outcome. Consequently, improvements in any of the foregoing deficiencies may improve the quality of these actions (e.g., reserve adjustments, treatment suggestions and claim reassignments) to the benefit of the claimant and the insuring entity.

SUMMARY

A computer system is disclosed which includes a data storage device. Functions performed by the data storage module include receiving, storing and providing access to historical claim data. A computer processor may execute program instructions and retrieve the historical claim data from the data storage device, while a memory, coupled to the computer processor, stores program instructions for execution by the computer processor.

A categorical aggregation component includes program instructions stored in the program memory, and provides categorized and aggregated historical claim data by identifying claim categories based on the historical claim data, where each of the one or more claim categories associated with a respective set of claim characteristics, identifying claims of the historical claim data associated with one of the claim categories, assigning each identified claim to one of a plurality of total severity ranges based on the total severity of the identified claim, and determining an average cost per claim year for claims of each total severity range when executed by the computer processor.

The computer system also includes a communication device, coupled to the computer processor, to output the categorized and aggregated historical claim data including the average cost per claim year for claims of each total severity range.

According to some embodiments, a computer system includes a data storage device for receiving, storing, and providing access to categorized and aggregated historical claim data, a computer processor for executing program instructions and for retrieving the categorized and aggregated historical claim data from the data storage device, and a memory, coupled to the computer processor, for storing program instructions for execution by the computer processor. A claim evaluation component includes program instructions stored in the program memory. The claim evaluation component is for receiving claim data of a current claim, identifying a pre-defined claim category based on the current claim data, calculating an estimated cost of the current claim for each of a plurality of outcome scenarios based on historical claim data associated with the pre-defined claim category, and determining a likelihood associated with each of the plurality of outcome scenarios based on the categorized and aggregated historical claim data associated with the pre-defined claim category when executed by the computer processor.

An output device, coupled to the computer processor, may present a graphical representation of the estimated cost and the likelihood associated with each of the plurality of outcome scenarios. The computer processor generates the graphical representation in accordance with program instructions in the program memory and executed by the computer processor.

With these and other advantages and features that will become apparent, embodiments may be more clearly understood by reference to the following detailed description, the appended claims, and the drawings attached hereto.

BRIEF DESCRIPTION OF THE DRAWINGS

FIG. 4 illustrates categorized and aggregated historical claim cost data according to some embodiments.

FIG. 5 illustrates categorized and aggregated historical claim count data according to some embodiments.

FIG. 8 is a outward view of a representative interface to receive current claim data according to some embodiments.

FIG. 9 is a graphical representation of graphical representation of an estimated cost and a likelihood associated with each of a plurality of outcome scenarios for a first claim category according to some embodiments.

DETAILED DESCRIPTION

Figure 1:
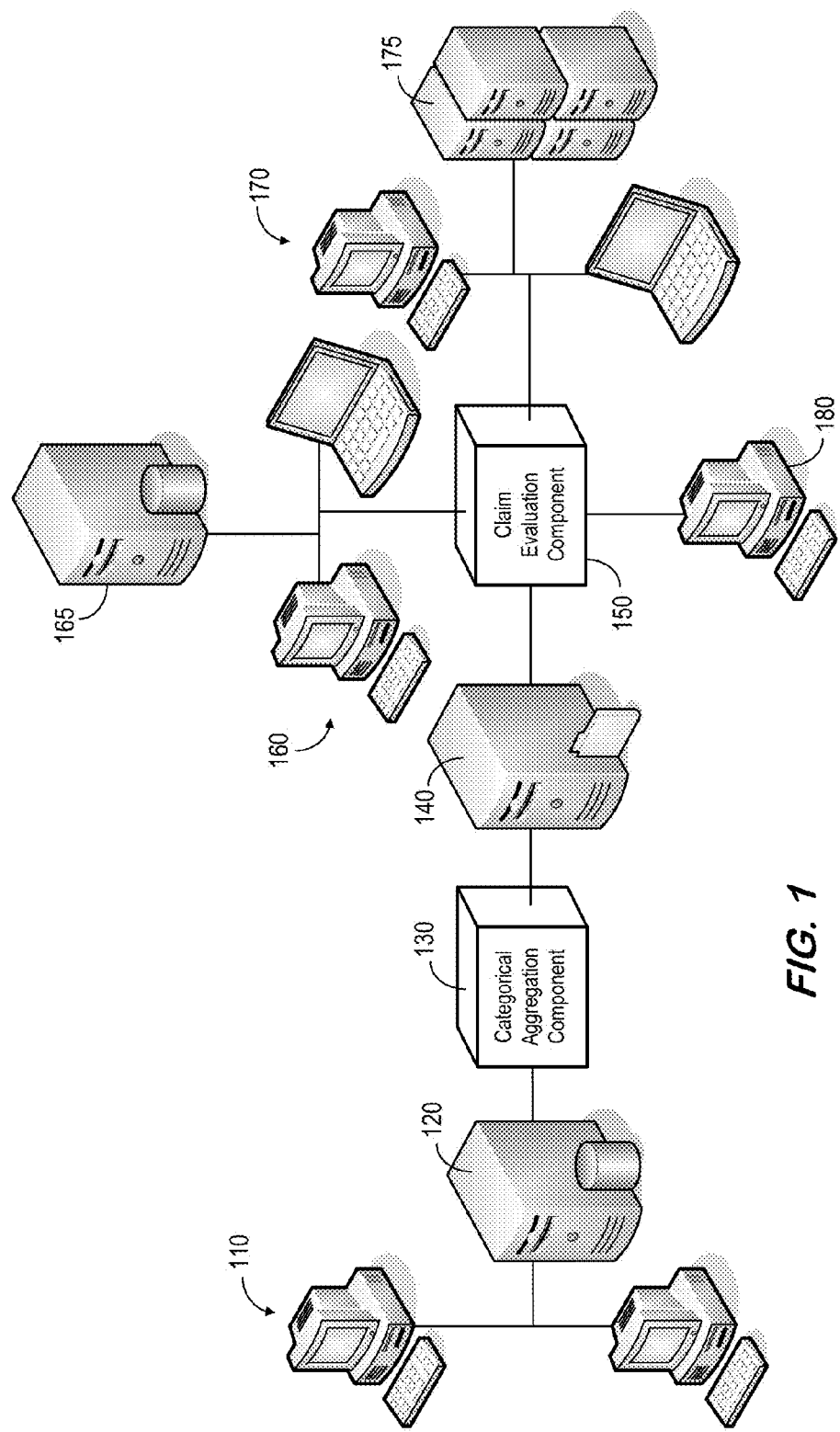
FIG. 1 illustrates a system architecture within which some embodiments may be implemented.

FIG. 1 illustrates system architecture 100 within which some embodiments may be implemented. Although the devices of architecture 100 are depicted as communicating via dedicated connections, it should be understood that all illustrated devices may communicate to one or more other illustrated devices through any number of other public and/or private networks, including but not limited to the Internet. Two or more of the illustrated devices may be located remote from one another and may communicate with one another via any known manner of network(s) and/or a dedicated connection. Moreover, each device may comprise any number of hardware and/or software elements suitable to provide the functions described herein as well as any other functions. Other topologies may be used in conjunction with other embodiments.

According to the example of FIG. 1, data entry terminals 110 receive claim data associated with various insurance claims. The foregoing description provides examples relating to medical insurance claims but embodiments are limited thereto. Data entry terminals 110 may be operated by a billing entity (e.g., a hospital, a physician's office, a pharmacy) or by a claims processor entering data received from a billing entity. Any number of data entry terminals may be employed to receive claim data according to some embodiments. The claim data may be generated and received using any systems that are or become known.

The claim data may include patient identification information, a service date, a description (e.g., of a procedure or a drug), a billing code (CPT ICD-9, Rev Codes, HCPCS), and a cost. The claim data may include any other suitable information related to a claim. Examples include patient height, patient weight, health risks and diagnosis.

The claim data is received and stored by data warehouse 120. Any number or type of data storage systems may store the claim data in any suitable manner according to some embodiments. Non-exhaustive examples include a relational database system, a spreadsheet, and any other data structure that is amenable to parsing.

Categorical aggregation component 130 receives the claim data (hereinafter referred to as "historical claim data") from data warehouse 120. Categorical aggregation component 130 categorizes and aggregates the historical claim data according to some embodiments. Detailed examples of this operation are provided below. Briefly, categorical aggregation component 130 identifies claim categories based on the historical claim data, where each of the one or more claim categories associated with a respective set of claim characteristics.

Claims of the historical claim data which are associated with one of the claim categories are identified, each identified claim is assigned to one of a plurality of total severity ranges based on the total severity of the identified claim, and an average cost per claim year is determined for claims of each total severity range.

Categorical aggregation component 130 may comprise any combination of hardware and/or processor-executable instructions stored on a tangible medium. According to some embodiments, categorical aggregation component 130 is an component of data warehouse 120 or data storage device 140.

Data storage device 140 may comprise any entity to store data, including a simple file server. In the illustrated embodiment, data storage device 140 receives and stores data output by categorical aggregation component 130. Specifically, data storage device 140 may store categorized and aggregated historical claim data including the average cost per claim year for claims of each total severity range.

Claim evaluation component 150 may access the categorized and aggregated historical claim data of data storage device 140. Claim evaluation component 150 is for receiving claim data of a current claim, identifying a pre-defined claim category based on the current claim data, calculating an estimated cost of the current claim for each of a plurality of outcome scenarios based on historical claim data associated with the pre-defined claim category, and determining a likelihood associated with each of the plurality of outcome scenarios based on the categorized and aggregated historical claim data associated with the pre-defined claim category when executed by the computer processor. Detailed examples of the foregoing according to some embodiments are provided below.

Claim evaluation component 150 may comprise any combination of hardware and/or processor-executable instructions stored on a tangible medium. According to some embodiments, claim evaluation component 150 is a component of data storage device 140 or of one or more of adjuster terminals 160.

Adjuster terminals 160 may present a graphical representation of the estimated cost and the likelihood associated with each of the plurality of outcome scenarios. Graphical representations according to some embodiments will be described in detail below. An adjuster may view the graphical representation and adjust insurance reserves specified within reserve database server 165. An adjuster may also or alternatively suggest treatment options, forward a claim to medical personnel, forward a claim to a claim processing department, and/or re-assign a claim based on the information presented by the graphical representation.

Medical personnel terminals 170 may receive a claim forwarded by adjuster terminals 160 as described above, and/or may receive a graphical representation of the estimated cost and the likelihood associated with each of the plurality of outcome scenarios from claim evaluation component 150. Terminals 170 may be operated by medical personnel to provide medical services associated with the claim based on the graphical representation. Such services may be facilitated using medical applications provided by medical application server 175.

Claim processing terminal 180 may also receive a graphical representation of the estimated cost and the likelihood associated with each of the plurality of outcome scenarios from claim evaluation component 150. A claim processor may operate terminal 180 to direct medical and financial processing of the claim based on the information presented by the graphical representation. As described above, claim processing terminal 180 may also receive a claim for processing from an adjuster terminal 160 based on the information presented by the graphical representation.

It should be noted that embodiments are not limited to the devices illustrated in FIG. 1. Each device may include any number of disparate hardware and/or software elements, some of which may be located remotely from one another. Functions attributed to one device may be performed by one or more other devices in some embodiments. The devices of system 100 may communicate with one another (and with other non-illustrated elements) over any suitable communication media and protocols that are or become known.

Figure 2:
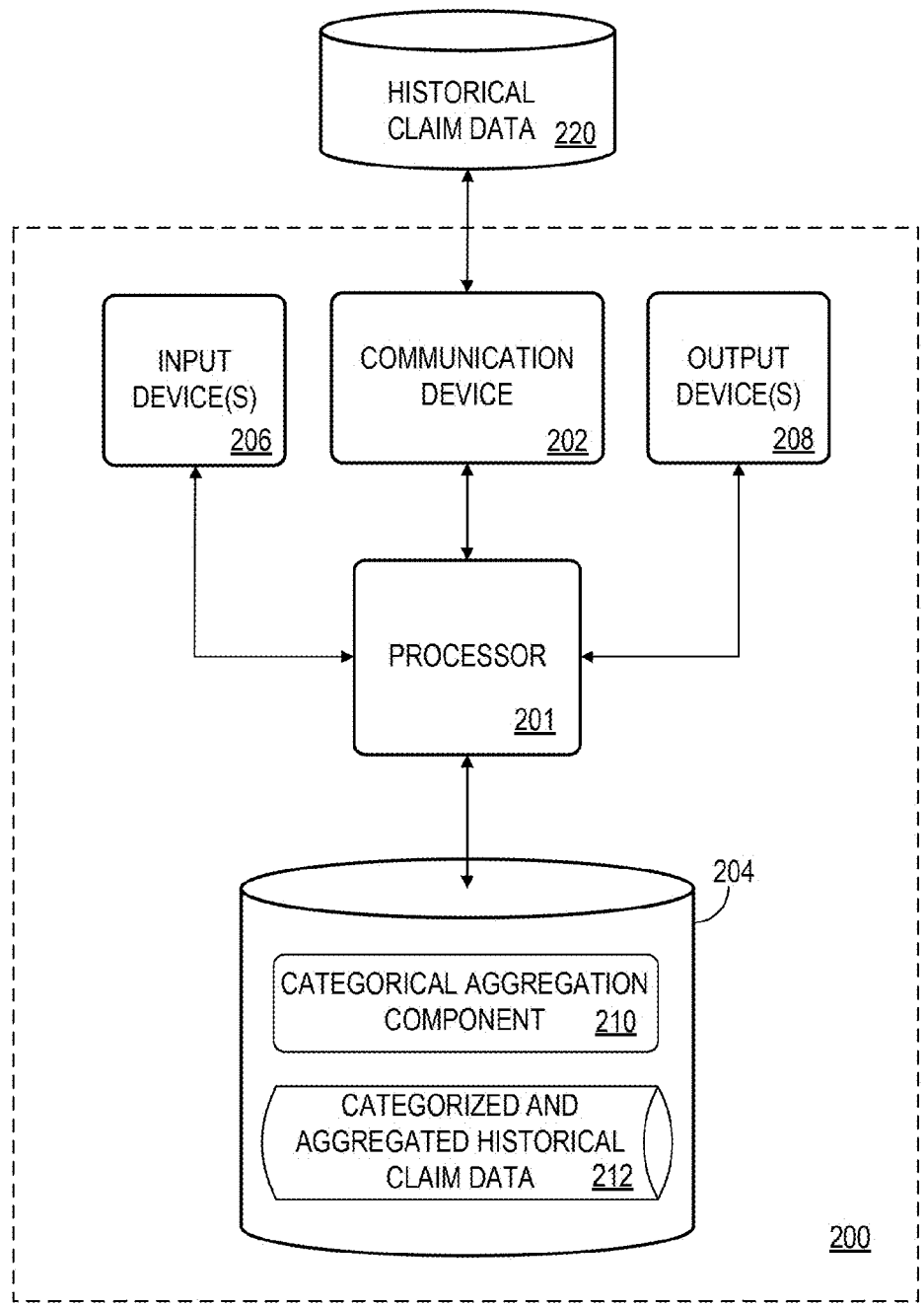
FIG. 2 is a partial functional block diagram of a computer system provided in accordance with some embodiments.

FIG. 2 is a block diagram of computer system 200 according to some embodiments.

Computer system 200 may perform the functions attributed above to categorical aggregation component 130. Computer system 200 includes computer processor 201 operatively coupled to communication device 202, data storage device 204, one or more input devices 206 and one or more output devices 208. Communication device 202 may facilitate communication with external devices. Input device(s) 206 may comprise, for example, a keyboard, a keypad, a mouse or other pointing device, a microphone, knob or a switch, an infra-red (IR) port, a docking station, and/or a touch screen. Input device(s) 206 may be used, for example, to enter information into computer system 200. Output device(s) 208 may comprise, for example, a display (e.g., a display screen) a speaker, and/or a printer.

Data storage device 204 may comprise any appropriate information storage device, including combinations of magnetic storage devices (e g, magnetic tape and hard disk drives), optical storage devices, and/or semiconductor memory devices such as Random Access Memory (RAM) devices and Read Only Memory (ROM) devices.

Data storage device 204 stores program instructions for execution by processor 201. Categorical aggregation component 210 may comprise a set of such instructions, and may be executed by processor 201 to cause system 200 to operate as described above with respect to categorical aggregation component 130 of FIG. 1. This operation may initially include operation of communication device 202 to retrieve historical claim data stored by external data storage device 220. In some embodiments, and as described with respect to FIG. 1, data storage device 220 may comprise a data warehouse.

Data storage device 204 also stores categorized and aggregated historical data 212, which may comprise the result of executing categorical aggregation component 210. Categorized and aggregated historical data 212 may be output via communication device 202 to an external storage device such as storage device 220 or storage device 140 of FIG. 1.

Categorized and aggregated historical data 212 may also or alternatively be output to claim evaluation component 150 or adjuster terminals 160 for consumption thereby according to some embodiments.

Figure 3:
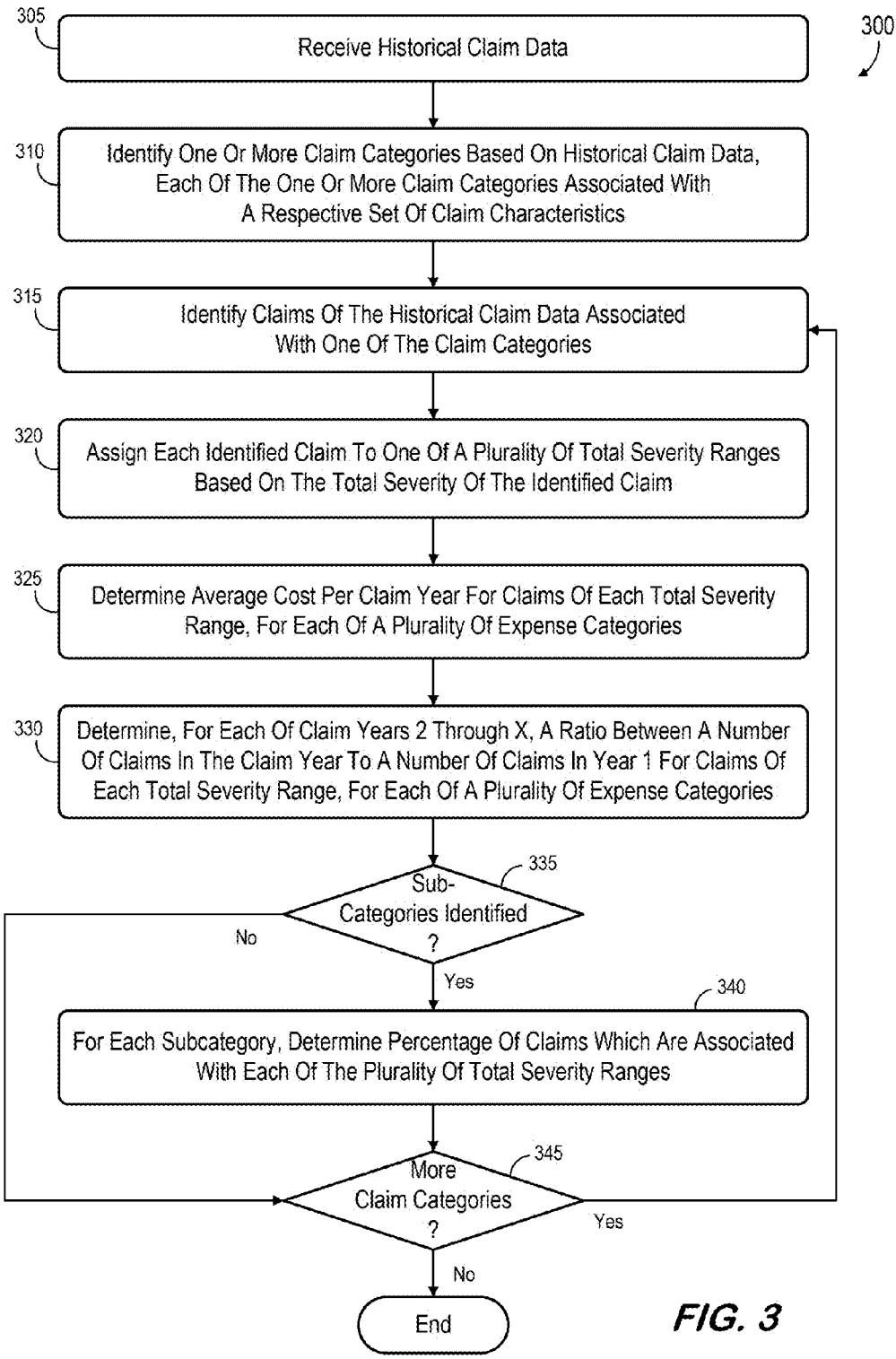
FIG. 3 is a flow diagram of a process according to some embodiments.

FIG. 3 is a flow diagram of process 300 according to some embodiments. Various elements of system architecture 100 and/or computer system 200 may execute process 300 according to some embodiments. Process 300 may be embodied within program instructions of categorical aggregation component 210 of computer system 200, but embodiments are not limited thereto.

Process 300 and all other processes mentioned herein may be embodied in processor-executable program instructions read from one or more computer-readable media, such as a floppy disk, a CD-ROM, a DVD-ROM, a Zip™ disk, and a magnetic tape, and then stored in a compressed, uncompiled and/or encrypted format. In some embodiments, hard-wired circuitry may be used in place of, or in combination with, program instructions for implementation of processes according to some embodiments. Embodiments are therefore not limited to any specific combination of hardware and software.

Initially, at 305, historical claim data is received. As described above, historical claim data may include patient identification information, a service date, a description, a billing code, a cost, and any other suitable information that is or becomes known. The historical claim data may be received from systems of a single operating entity (e.g., a single insurance company), from several operating entities, from relevant literature (e.g., studies, reports, trials), and from any other claim data source.

Next, at 310, one or more claim categories are identified based on the received historical claim data. Each of the one or more claim categories is associated with a respective set of claim characteristics. According to some embodiments, the historical claim data is filtered based on one or more characteristics (described below) prior to identifying the claim categories. Such filtering may provide improved results and/or speed processing by removing less relevant data from the historical data.

According to some embodiments, a claim category is identified at 310 by first determining a set of claim characteristics which define claims of particular interest. The set of characteristics may be determined based on scientific literature, the historical claim data, medical expertise, claim adjusting expertise and/or professional actuarial experience. For example, the present inventors have discovered that a significant percentage of non-traumatic back surgery claims exhibit high total severity while a significant percentage of non-traumatic back surgery claims exhibit low total severity. Accordingly, these types of claims are believed to form a category of claims which may be amenable to subsequent analysis according to some embodiments. A set of claim characteristics (e.g., billing code, procedure type, co-morbidities, individual claimant data (e.g., age, industry, work type)) which define non-traumatic back surgery claims is therefore determined at 310.

Next, claims of the historical claim data which exhibit the determined set of claim characteristics are identified, and it is determined whether the number of the identified claims exceeds a statistical significance threshold. This check may be desirable to insure that the number of claims is suitable to produce statistically relevant aggregations that may be reliably employed in subsequent analysis.

If the number of claims exceeds the statistical significance threshold, a total severity statistical profile is determined based on a total severity of each of the first claims. If the total severity statistical profile meets predefined profile criteria, a claim category is created and is associated with the determined set of claim characteristics. The total severity statistical profile and the predefined profile criteria may be defined and determined based on known statistical techniques, with the goal of ensuring that the total severities of the identified claims are suitable for analysis as will be described below.

According to some embodiments, one or more subcategories may be defined based on an identified claim category. Each subcategory of a category is associated with a set of characteristics which is a subset of the set of characteristics associated with the category. Identification of subcategories may proceed according to the above example of category definition. For example, the present inventors have identified the subcategories "cervical" and "lumbar" of the category "non-traumatic back surgery", the sub-subcategories "fusion" and "no fusion" of the subcategory "lumbar surgery", and the sub-subcategories "fusion" and "no fusion" of the subcategory "cervical surgery". Each of the categories, subcategories and sub-subcategories correspond to a respective procedure code in some embodiments, which facilitates the identification of related historical claim data.

Identification of claim categories may therefore proceed iteratively, where a first set of characteristics is initially identified and then refined based on the claim data of associated claims. Moreover, any statistical profile criteria may be used to evaluate the suitability of a claim category and its underlying claim characteristics.

Claims associated with one of the claim categories are identified at 315. Such identification may include comparing claims of the historical data with a set of claim characteristics associated with the subject claim category. Each identified claim is then assigned to one of a plurality of severity ranges based on its total severity at 320.

The foregoing example uses the severity ranges "Bottom 20%", "Middle 60%" and "Top 20%", but embodiments are not limited thereto. Accordingly, based on their total severities, each claim of the claim category is assigned to one of these three severity ranges at 320.

Next, at 325, an average cost per claim year is determined for the claims of each total severity range. According to the present example, the determined average cost per claim year is divided amongst expense categories (e.g., Hospital, Physician, Prescription, Other). FIG. 4 illustrates the calculation of an average cost per claim year for hospital expenses for claims of the "Top 20%" total severity range. As shown, these claims are associated with a claim category "non-traumatic lumbar surgery". The 1998 total for claim year 2, for example, represents an average hospital cost in 1998 for claims of the Top 20% total severity range for which 1998 was the second claim year.

Returning to process 300, some embodiments further determine, for claims existing in each of claim years 2 through X, a ratio between a number of claims in the claim year to a number of claims in year 1. These ratios are determined for each expense category and for each range of total severities.

FIG. 5 illustrates calculation of the above-described ratios for each of claim years 2 through X, for the "Middle 60%" total severity range and the hospital expense category. The upper table provides a number of claims within the Middle 60% total severity range which did not settle (i.e., arose in a non-settlement jurisdiction and/or exhibited actual medical closure) and for which a hospital expense was incurred in a given claim year. Again, this information is determined from the historical claim data associated with claims falling under the "non-traumatic lumbar surgery" claim category.

The lower table shows the ratios determined at 330 according to some embodiments. The ratios for a given claim year are determined by dividing a claim count during the claim year by a corresponding claim count during year 1. For example, the ratio for year 2 (77.8%) is equal to the claim count for claim year 2 (i.e., 1265) divided by the claim count in claim year 1 for those claims which have matured to at least year 2 (i.e., 1810−183=1627). Similarly, the ratio for year 4 (35.0%) is equal to the claim count for claim year 4 (i.e., 432) divided by the claim count in claim year 1 for those claims which have matured to at least year 4 (i.e., 1810−183−203−189=1235).

Flow continues from 335 to 340 if any subcategories have been identified. For each such subcategory, a determination is made as to what percentage of the subcategory's claims is associated with each of the plurality of total severity ranges. By definition, the claims of the associated category are segmented according to the severity ranges (e.g., 20%/60%/20%), but at 340 it is determined what percentage of the subcategory's claims fall in each of the Top 20%, Middle 60% and Bottom 20% ranges. For example, it may be determined that, in the "fusion" subcategory of the "non-traumatic lumbar surgery" category, 40% of the claims are claims which are associated with the Top 20% severity range of the "non-traumatic lumbar surgery" category, 52% of the claims are claims which are associated with the Middle 60% severity range, and 8% of the claims are claims which are associated with the Bottom 20% severity range.

If additional claim categories exist, flow returns to 315 from 345 and continues as described above with respect to another claim category. Otherwise, flow terminates.

The information determined at 325, 330 and 340 of process 300 is referred to herein as categorized and aggregated historical claim data. Embodiments may determine less, more and/or different data than that described above. The categorized and aggregated historical claim data may be output and subsequently used to determine claim severities and associated likelihoods according to some embodiments. Examples of these determinations are set forth in detail below.

Figure 6:
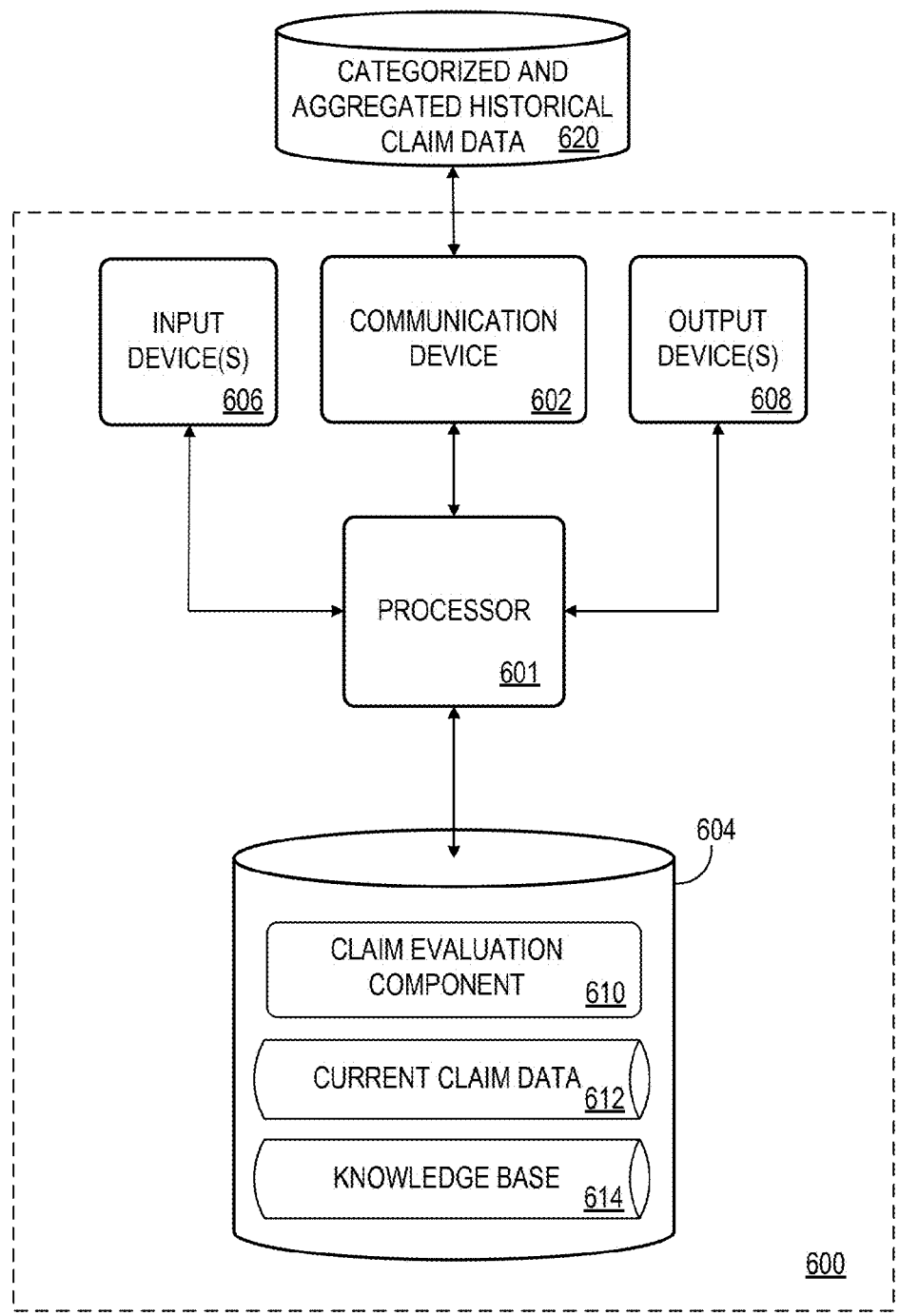
FIG. 6 is a partial functional block diagram of a computer system provided in accordance with some embodiments.

FIG. 6 is a block diagram of computer system 600 according to some embodiments. Computer system 600 may perform the functions attributed above to claim evaluation component 150. Computer system 600 includes computer processor 601, which is operatively coupled to communication device 602, data storage device 604, one or more input devices 606 and one or more output devices 608. Communication device 602 may facilitate communication with external devices. Input device(s) 606 and output device(s) 608 may comprise any devices described above with respect to input device(s) 206 and output device(s) 208, but are not limited thereto.

Data storage device 604 may comprise any appropriate information storage device, including combinations of magnetic storage devices (e.g., magnetic tape and hard disk drives), optical storage devices, and/or semiconductor memory devices such as RAM devices and ROM devices.

Data storage device 604 stores program instructions for execution by processor 600, such as claim evaluation component 610. Claim evaluation component 610 may be executed by processor 601 to cause system 600 to operate as described above with respect to claim evaluation component 150 of FIG. 1. Communication device 602 may retrieve categorized and aggregated historical claim data stored by external data storage device 620 in accordance with this operation. The categorized and aggregated historical claim data may have been generated in accordance with process 300 or any other suitable process. In some embodiments, and as described with respect to FIG. 1, data storage device 620 comprises a file server.

Data storage device 604 may also store current claim data 612 to be evaluated in view of the categorized and aggregated historical data of device 620. This evaluation may incorporate data from knowledge base 616. For example, knowledge base 616 may provide data relating to co-morbidities and or other factors which may affect the total severity of a claim outcome and/or a likelihood of that outcome.

Figure 7:
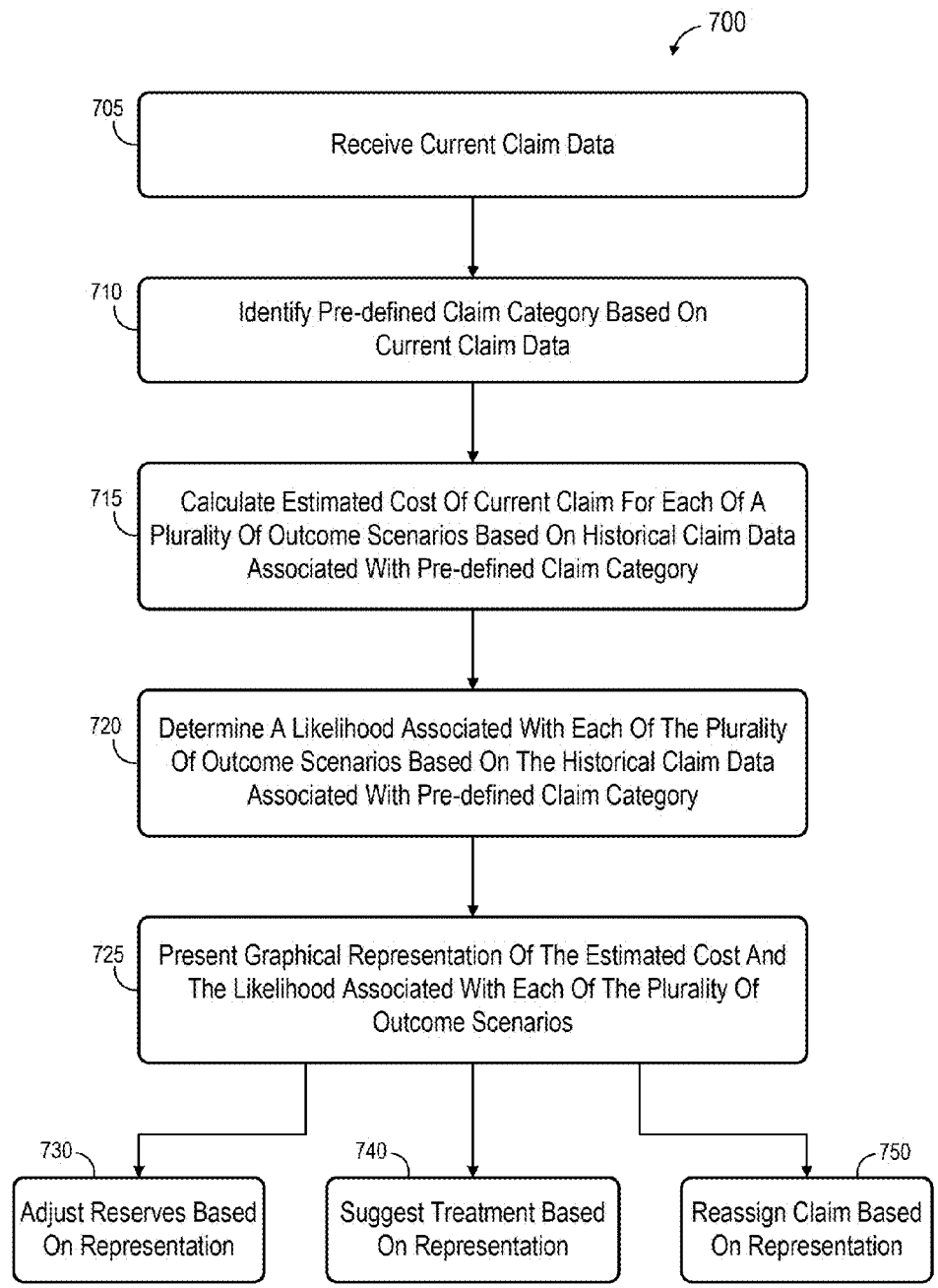
FIG. 7 is a flow diagram of a process according to some embodiments.

FIG. 7 is a flow diagram of process 700 to evaluate claim outcomes according to some embodiments. Process 700 may be embodied within program instructions of claim evaluation component 610 of computer system 600, but embodiments are not limited thereto.

Current claim data is received at 705. The current claim data may be received from any storage device, such as but not limited to a data warehouse. Some or all of the current claim data may be received from an adjuster via a user interface.

FIG. 8 is an outward view of user interface 800 to receive current claim data according to some embodiments.

According to some embodiments, an adjuster operates computer system 600 to execute claim evaluation component 610. In response, output device 608 displays user interface 800 to the adjuster.

User interface 800 includes fields that may be pre-populated based on current claim data 612 stored in system 600. The adjuster may also or alternatively populate the fields with data received from disparate sources, such as other claim review databases, physical files, etc. Notably for purposes of the present examples, user interface 800 includes fields for indicating co-morbidities (i.e., obesity, drugs/alcohol/psych), surgery type (i.e., "Fusion?", lumbar), and projected annual expenditures for various expense categories (i.e., (H)ospital, (P)hysician, p(R)escription, and Other Medical (OM)). Tables are also provided for entering other known or expected miscellaneous exposure information that may be used to enhance the subsequent evaluation.

At 710, a pre-defined claim category is identified based on the received current claim data. It will be assumed that the pre-defined claim category is a claim category determined according to 310 of process 300, but embodiments are not limited thereto. In some embodiments of 710, it is determined that the current claim data exhibits a set of characteristics that is associated with a pre-defined claim categories. With respect to the present example, the pre-defined claim category is the "non-traumatic lumbar surgery" category described above.

Next, at 715, an estimated cost of the current claims is calculated for each of a plurality of outcome scenarios based on historical claim data associated with the pre-defined claim category. The estimated cost may be determined based on categorized and aggregated historical data in some embodiments. For example, the estimated cost attributable to hospital expenses for a high-cost (e.g., Top 20% severity) outcome scenario may be determined based on the categorized and aggregated historical data of FIG. 4.

FIG. 9 illustrates graphical representation 900 for purposes of explaining some embodiments of 715. Graphical representation 900 may be presented to an adjuster at 725 of process 700 as will be described below.

In the present example, the annual hospital cost for the high-cost outcome scenario after the first year is determined by first calculating the average of the average costs shown in FIG. 4. This average is multiplied by the factors associated with any existing co-morbidities. Specifically, the average (i.e., $11,161) is multiplied by the obesity factor (1.1252) and the psych factor (1.1396) to determine an annual cost (i.e., $14,311). This annual cost is used in representation 900 unless a greater projected annual spend is received in 705 (e.g., from an adjuster), in which case the projected annual spend is used as the annual cost. The corresponding first year hospital costs are determined to be equal to the annual cost.

The total attributable to hospital costs is the present value of the annual costs over the listed claim duration (i.e., 34.96 years) and at the listed discount rate (i.e., 5.00%), plus the first year costs. Embodiments are not limited to the foregoing calculations.

The remaining rows of the Hospital Costs portion of representation 900 may be completed as described based on categorized and aggregated historical claim data. However the data used to complete the rows includes average costs per claim year for claims in the subject category and in the severity range (i.e., Middle 60%, Bottom 20%) corresponding to the row to be completed. The Physician Costs portion, Drug Costs portion, and Other Medical Costs portion of representation 900 may be similarly completed using similar categorized and aggregated historical data, albeit associated with the appropriate expense category and severity range.

The estimated cost of the current claim for each of the six outcome scenarios is shown in the Total Reserve column of representation 900. The Total Reserve for a given outcome scenario is determined by summing all the Total columns in the row associated with the outcome scenario. Again, embodiments are not limited to the specific calculations set forth herein.

Returning to FIG. 7, a likelihood associated with each of the plurality of outcome scenarios is determined at 720. The likelihood is determined based on the historical claim data associated with the subject claim category.

Figure 10:
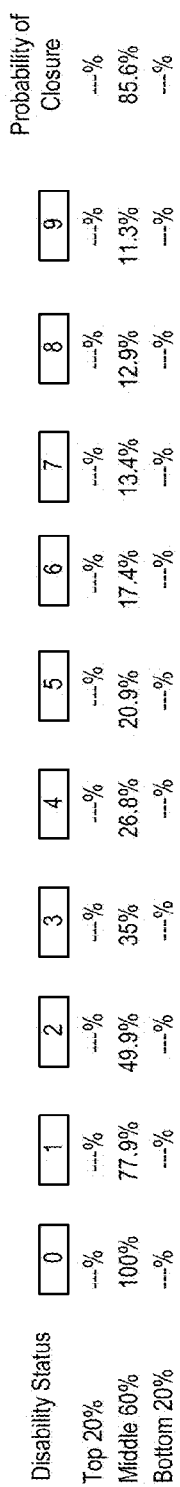
FIG. 10 illustrates categorized and aggregated historical claim count data according to some embodiments.

The LHood column of FIG. 9 indicates likelihoods calculated according to some embodiments of 720. The likelihoods may be calculated based on categorized and aggregated historical claim data such as that illustrated in FIG. 5. FIG. 10 illustrates previously-determined ratios between a number of claims in a given claim year to a number of claims in year 1. These ratios may comprise the ratios corresponding to a single expense category. In embodiments such as that depicted in FIG. 10, the ratio illustrated for a given claim year and severity range is the maximum of the ratios calculated for each expense category for the given claim year and severity range. Accordingly, some but not all of the ratios depicted in FIG. 10 are identical to those shown in FIG. 5 in association with the hospital expense category.

Continuing with the determination at 720, a probability of closure is determined for each severity range. The probability of closure shown in FIG. 10 is calculated as $(1 - \text{Ratio}_{Yr9}/\text{Ratio}_{currentYr})$. Embodiments are not limited to this calculation.

For scenarios associated with no Natural Medical Closure (i.e., scenarios 1-3), the likelihoods are calculated for each severity range as (% $\text{claims}_{severityRange}$(1−Probability of $\text{Closure}_{SeverityRange}$)). Conversely, for scenarios associated with a Natural Medical Closure (i.e., scenarios 4-6), the likelihoods are calculated for each severity range as (% $\text{claims}_{SeverityRange}$ (Probability of $\text{Closure}_{SeverityRange}$)). In a case that the current claim is associated with a subcategory of the identified claim category, the values % $\text{claims}_{SeverityRange}$ may be those percentages generated at 340 of process 300. According to the illustrated example, the percentages corresponding to the Top 20%, Middle 60% and Bottom 20% severity ranges for the "fusion" subcategory are 40%, 52% and 8%, respectively. Other percentages may be employed in a case that current claim is associated with a "no fusion" subcategory.

A graphical presentation of the estimated cost (i.e., Total Reserve) and likelihood (i.e., LHood) of each outcome scenario is presented at 725. The graphical representation may comprise representation 900, but embodiments are not limited thereto.

Figure 11:
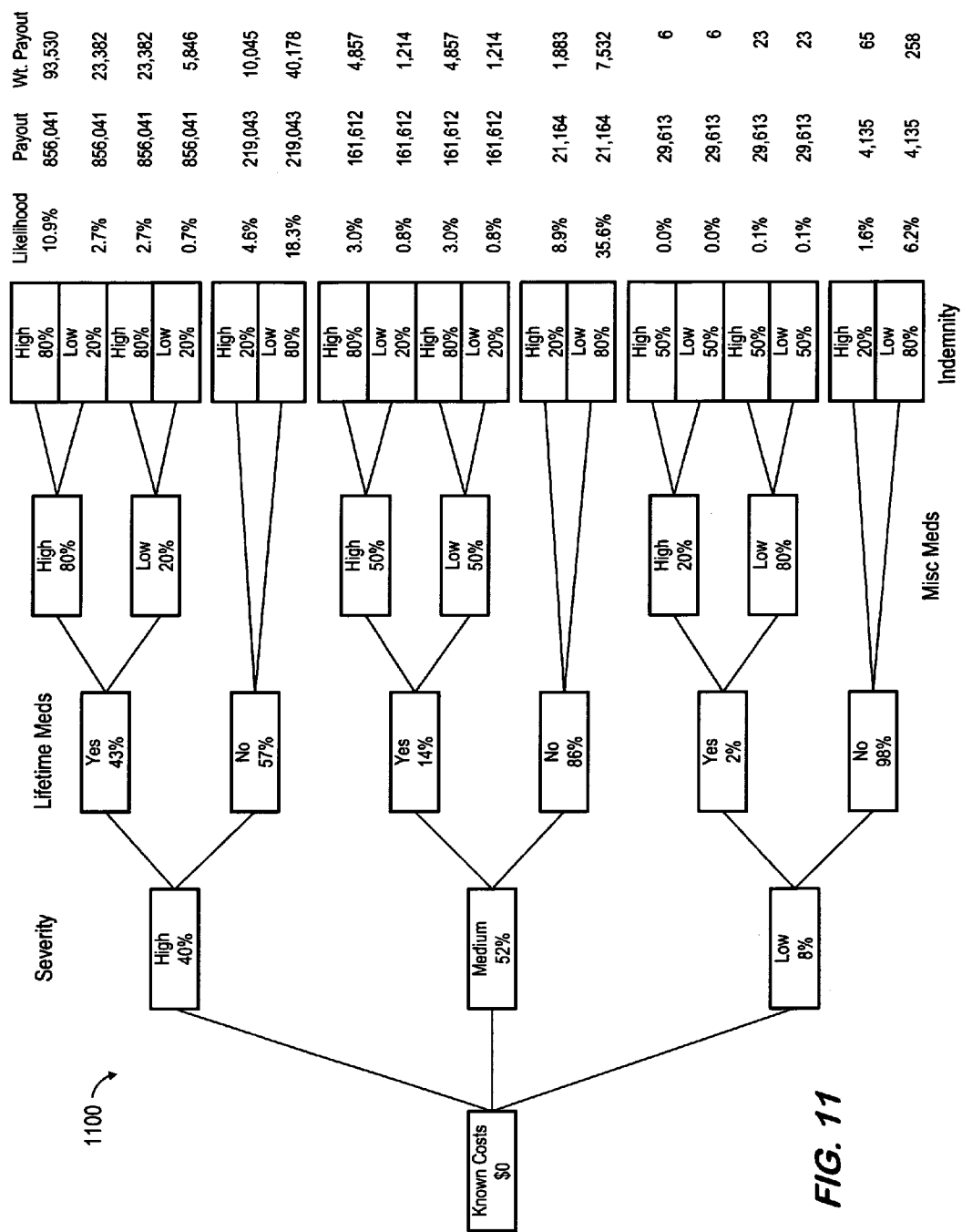
FIG. 11 is a graphical representation of an estimated cost and a likelihood associated with each of a plurality of outcome scenarios for the first claim category according to some embodiments.

FIG. 11 illustrates decision tree 1100 for presenting the costs and associated likelihoods in a graphical format. Tree 1100 also shows weighted payout amounts obtained by multiplying each associated likelihood and payout. The nodes of the tree represent default percentages based on the current claim data and the historical claim data. In some embodiments, an adjuster or other professional viewing tree 1100 may change these values to reflect his professional judgment of the claim, resulting in corresponding changes to the values in the Likelihood, Payout and Wt. Payout columns.

The presented graphical representation may improve the evaluation of potential claim outcomes. Accordingly, the quality of any actions taken based on the evaluation may also improve. As shown in FIG. 7, such actions may include adjusting reserves based on the representation (730), suggesting treatment based on the representation (740) and reassigning the claim based on the representation (750).

The embodiments described herein are solely for the purpose of illustration. Those in the art will recognize that other embodiments may be practiced with modifications and alterations limited only by the claims.

What is claimed is:

1. A computer system for estimating insurance claim severity, comprising:
   a first data storage device storing data relating to a plurality of insurance claims, the data comprising a plurality of characteristics associated with each of the plurality of insurance claims and total claim cost data associated with each of the claims;
   a computer processor in communication with the data storage device; and
   a program memory in communication with the computer processor, storing computer-readable instructions, which, when executed by the computer processor, cause the computer processor to:
      determine a first set of claim characteristics;
      determine a plurality of first claims of the plurality of insurance claims, the first claims each having the claim characteristics of the first set;
      determine a statistical profile of the claim cost data of the first claims based on the claim cost data associated with each of the first claims;
      determine whether the determined statistical profile meets profile criteria;
      responsive to determining that the determined statistical profile meets the profile criteria, associate the first set of claim characteristics with a first claim category;
      associate each of the first claims to one of a plurality of total cost ranges based on the total cost data associated with the first claims;
      determine an average cost per claim year associated with each of a plurality of expense categories for the first claims associated with each of the total cost ranges; and
      store in a second data storage device the determined average cost per claim year data; and
   a display device in communication with the second data storage device configured to display the determined average cost per claim year data.

2. The computer system of claim 1, wherein the computer-readable instructions, which, when executed by the computer processor, further cause the computer processor to:
   determine a second set of claim characteristics, the second set of claim characteristics being a subset of the first set of claim characteristics;
   identify second claims of the plurality of stored claims, the second claims having associated therewith the second set of claim characteristics;
   determine a statistical profile of the total cost data associated with the second claims;
   responsive to determining that the determined statistical profile meets the profile criteria, associate the second set of claim characteristics with a second claim category, the second claim category being a subcategory of the first claim category.

3. The computer system of claim 2, wherein the first claim category is non-traumatic back surgery, the second claim category is cervical, and further comprising a further second claim category being a subset of the first claim category, the further second claim category being lumbar.

4. The computer system of claim 3, further comprising subcategories fusion and no fusion of the second claim category lumbar.

5. The computer system of claim 3, further comprising subcategories fusion and no fusion of the second claim category cervical.

6. The computer system of claim 2, further comprising a claim evaluation component, the claim evaluation component comprising:
   a third data storage device storing data relating to one or more current insurance claims;
   a second computer processor in communication with the third data storage device;
   a second program memory in communication with the second computer processor, storing second computer-readable instructions, which, when executed by the second computer processor, cause the second computer processor to:
      based on the stored data relating to one of the current insurance claims, associate the current claim with one of the categories; and
      calculate, based on data from claims associated with the one of the categories, an estimated total cost of the one of the current insurance claims for each of a plurality of outcome scenarios; and
   a display device configured to display a graphical representation of the estimated total cost of the one of the current insurance claims for each of the plurality of outcome scenarios.

7. The computer system of claim 6, wherein a first one of the plurality of outcome scenarios comprises a first range of total cost; and a second one of the plurality of outcome scenarios comprises a second range of total cost lower than the first range of total cost.

8. The computer system of claim 6, wherein the second computer-readable instructions, when executed by the second computer processor, further cause the second computer processor to determine a likelihood associated with each of the outcome scenarios based on the claim data associated with the category associated with the one of the current claims.

9. The computer system of claim 6, further comprising an adjuster terminal display device in communication with the second computer processor, and wherein the second computer-readable instructions, when executed by the second computer processor, further cause the second computer processor to output to the adjuster terminal display device data indicative of an estimated cost and a likelihood associated with each of the outcome scenarios.

10. The computer system of claim 9, wherein an adjuster terminal is further configured to receive and execute adjuster instructions to perform one or more of: suggesting treatment options, forwarding the current claim to a medical personnel terminal, forwarding the current claim to a claim processing terminal, or re-assigning the current claim.

11. The computer system of claim 10, further comprising a medical personnel terminal, and a medical hardware server, wherein the medical personnel terminal is configured to receive the current claim forwarded by the adjuster terminal and to provide medical services associated with the current claim using medical application programs furnished by the medical hardware server.

12. A computer-implemented method for estimating insurance claim severity, comprising:
   accessing, by a computer processor, a first data storage device storing data relating to a plurality of insurance claims, the data comprising a plurality of characteristics associated with each of the plurality of insurance claims and total claim cost data associated with each of the claims;
   determining, by the computer processor, a first set of claim characteristics;

determining, by the computer processor, a plurality of first claims of the plurality of insurance claims, the first claims each having the claim characteristics of the first set;

determining, by the computer processor, a statistical profile of the claim cost data of the first claims based on the claim cost data associated with each of the first claims;

determining, by the computer processor, whether the determined statistical profile meets profile criteria;

responsive to determining that the determined statistical profile meets the profile criteria, associating, by the computer processor, the first set of claim characteristics with a first claim category;

associating, by the computer processor, each of the first claims to one of a plurality of total cost ranges based on the total cost data associated with the first claims;

determining, by the computer processor, an average cost per claim year associated with each of a plurality of expense categories for the first claims associated with each of the total cost ranges;

storing, in a second data storage device, the determined average cost per claim year data; and displaying, by a display device in communication with the second data storage, device, the determined average cost per claim year data.

13. The computer-implemented method of claim 12, further comprising:

determining by the computer processor a second set of claim characteristics, the second set of claim characteristics being a subset of the first set of claim characteristics;

identifying by the computer processor second claims of the plurality of stored claims, the second claims having associated therewith the second set of claim characteristics;

determining by the computer processor a statistical profile of the total CLAIM cost data associated with the second claims;

responsive to determining that the determined statistical profile meets the profile criteria, associating by the computer processor the second set of claim characteristics with a second claim category, the second claim category being a subcategory of the first claim category.

14. The computer-implemented method of claim 13, further comprising:

accessing by a computer processor of a claim evaluation component a third data storage device storing data relating to one or more current insurance claims;

based on the stored data relating to one of the current insurance claims, associating by the claim evaluation component computer processor the current claim with one of the categories;

calculating, by the claim evaluation component computer processor, based on data from claims associated with the one of the categories, an estimated total cost of the one of the current insurance claims for each of a plurality of outcome scenarios; and displaying by a display device a graphical representation of the estimated total cost of the one of the current insurance claims for each of the plurality of outcome scenarios.

15. The computer-implemented method of claim 14, further comprising:

outputting by the claim evaluation component computer processor to a display device of an adjuster terminal in communication data indicative of a estimated total claim cost and a likelihood associated with each of the outcome scenarios; and displaying by the adjuster terminal display device the data indicative of an estimated cost and a likelihood associated with each of the outcome scenarios.

16. The computer-implemented method of claim 15, further comprising:

receiving and executing, by the adjuster terminal, instructions to perform one or more of: suggesting treatment options, forwarding the current claim to a medical personnel terminal, forwarding the current claim to a claim processing terminal, or re-assigning the current claim.

17. The computer-implemented method of claim 16, further comprising:

receiving, by a medical personnel terminal, the current claim forwarded by the adjuster terminal; and providing, by the medical personnel terminal, medical services associated with the current claim using medical application programs furnished by a medical hardware server.

18. A non-transitory computer-readable medium having computer-readable instructions stored thereon, which instructions, when executed by a computer processor, cause the computer processor to:

access a first data storage device storing data relating to a plurality of insurance claims, the data comprising a plurality of characteristics associated with each of the plurality of insurance claims and total claim cost data associated with each of the claims;

determine a first set of claim characteristics;

determine a plurality of first claims of the plurality of insurance claims, the first claims each having the claim characteristics of the first set;

determine a statistical profile of the claim cost data of the first claims based on the claim cost data associated with each of the first claims;

determine whether the determined statistical profile meets profile criteria;

responsive to determining that the determined statistical profile meets the profile criteria, associate the first set of claim characteristics with a first claim category;

associate each of the first claims to one of a plurality of total cost ranges based on the total cost data associated with the first claims;

determine an average cost per claim year associated with each of a plurality of expense categories for the first claims associated with each of the total cost ranges; and output to a second data storage device, for storage, the determined average cost per claim year data.

19. The non-transitory computer-readable medium of claim 18, wherein the instructions, when executed by the computer processor, further cause the computer processor to:

determine a second set of claim characteristics, the second set of claim characteristics being a subset of the first set of claim characteristics;

identify second claims of the plurality of stored claims, the second claims having associated therewith the second set of claim characteristics;

determine a statistical profile of the total cost data associated with the second claims;

responsive to determining that the determined statistical profile meets the profile criteria, associate the second set of claim characteristics with a second claim category, the second claim category being a subcategory of the first claim category.

20. The non-transitory computer-readable medium of claim 19, wherein the first claim category is non-traumatic back surgery, the second claim category is cervical, and further comprising a further second claim category being a subset of the first claim category, the further second claim category being lumbar.

* * * * *